(12) United States Patent
Zinnanti

(10) Patent No.: US 9,101,363 B2
(45) Date of Patent: Aug. 11, 2015

(54) CAUTERY ELECTRODE WITH MULTI-CHANNEL INSULATED SHAFT

(71) Applicant: William J. Zinnanti, Santa Cruz, CA (US)

(72) Inventor: William J. Zinnanti, Santa Cruz, CA (US)

(*) Notice: Subject to any disclaimer, the term of this patent is extended or adjusted under 35 U.S.C. 154(b) by 195 days.

(21) Appl. No.: 13/706,242

(22) Filed: Dec. 5, 2012

(65) Prior Publication Data

US 2014/0046321 A1  Feb. 13, 2014

Related U.S. Application Data

(60) Provisional application No. 61/681,626, filed on Aug. 10, 2012.

(51) Int. Cl.
*A61B 18/14* (2006.01)

(52) U.S. Cl.
CPC ............ *A61B 18/14* (2013.01); *A61B 18/1482* (2013.01); *A61B 18/1402* (2013.01); *A61B 2018/144* (2013.01); *A61B 2018/1407* (2013.01); *A61B 2018/1417* (2013.01); *A61B 2218/002* (2013.01); *A61B 2218/007* (2013.01)

(58) Field of Classification Search
USPC .................................... 606/41, 32, 27–28, 45
See application file for complete search history.

(56) References Cited

U.S. PATENT DOCUMENTS

| | | | |
|---|---|---|---|
| 1,813,902 A | 1/1928 | Bovie | |
| 2,888,928 A | 4/1957 | Seiger | |
| 3,828,780 A | 8/1974 | Morrison | |
| 4,562,838 A | 1/1986 | Walker | |
| 5,224,944 A | 7/1993 | Elliott | |
| 5,234,428 A | 8/1993 | Kaufman | |
| 5,242,442 A | 9/1993 | Hirschfeld | |
| 5,836,944 A | 11/1998 | Cosmescu | |
| 6,146,353 A | 11/2000 | Platt | |
| 7,329,253 B2 * | 2/2008 | Brounstein et al. | 606/41 |
| 8,057,470 B2 | 11/2011 | Lee | |
| 2004/0024397 A1 * | 2/2004 | Griffin et al. | 606/41 |
| 2007/0106292 A1 * | 5/2007 | Kaplan et al. | 606/41 |
| 2010/0205802 A1 * | 8/2010 | Huseman | 29/825 |
| 2013/0012934 A1 * | 1/2013 | Manwaring et al. | 606/29 |

\* cited by examiner

*Primary Examiner* — Paula J Stice
(74) *Attorney, Agent, or Firm* — Cardinal Law Group

(57) ABSTRACT

The invention provides a cautery electrode comprising an insulated shaft and a conductive element. The insulated shaft includes first and second channels disposed within the shaft and extending the length of the shaft. The conductive element comprises a tip segment, a mid-segment, and an electrical contact segment. The conductive element is disposed within the first channel such that the tip segment extends from a distal end of the shaft, the mid-segment is within the shaft, and the electrical contact segment extends from a proximal end of the shaft. A cautery system includes the cautery electrode, a cautery handpiece, a length of tubing, and a connector having first, second, and third connection points. The cautery electrode and the cautery handpiece are removably attached to the connector at the first and second connection points, and the length of tubing is attached to the connector at the third connection point.

20 Claims, 2 Drawing Sheets

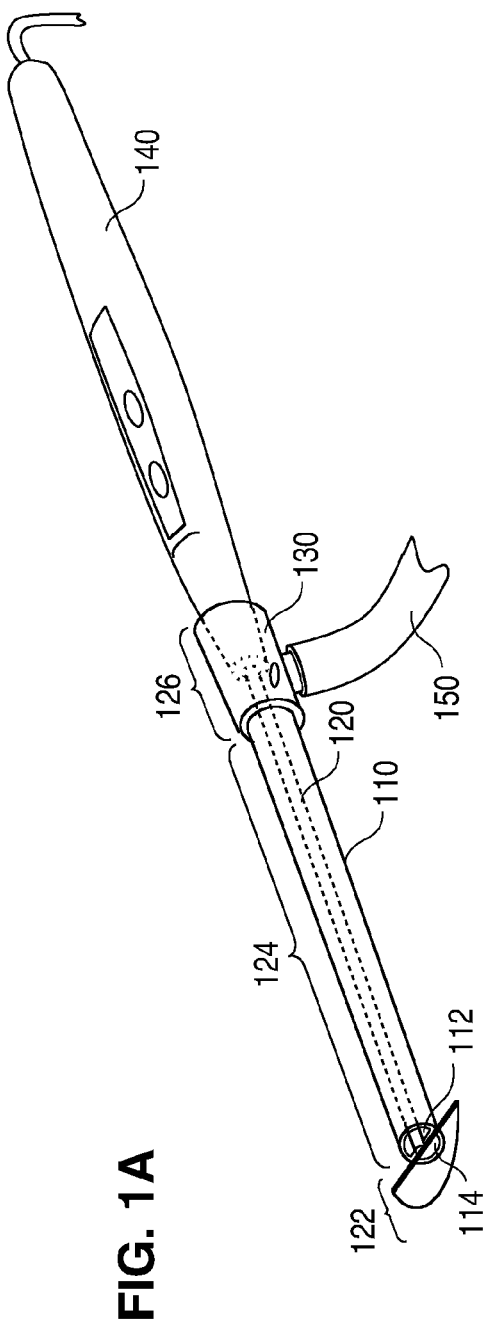
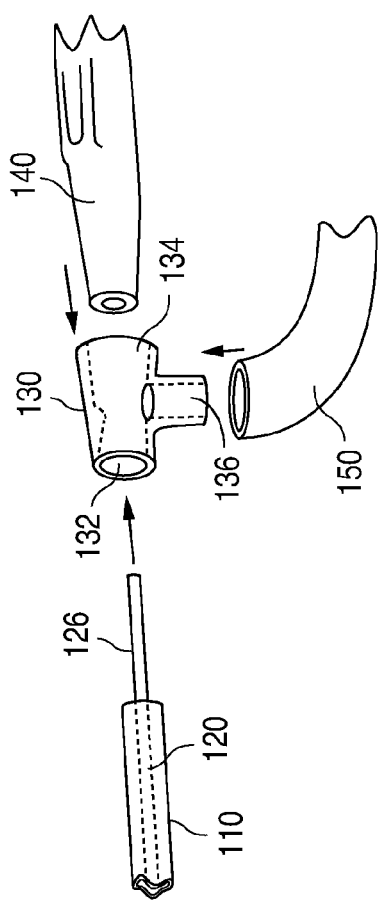
FIG. 1A
FIG. 1B
FIG. 1C

CAUTERY ELECTRODE WITH MULTI-CHANNEL INSULATED SHAFT

CROSS REFERENCE TO RELATED APPLICATION

This application claims the benefit of U.S. Provisional Application No. 61/681,626, filed Aug. 10, 2012, which is incorporated herein by reference in its entirety for all purposes.

TECHNICAL FIELD

This invention relates generally to surgical instruments. More particularly, the invention relates to a cautery electrode with a multi-channel insulated shaft and a cautery electrode system that provide smoke removal during surgical operations.

BACKGROUND OF THE INVENTION

In certain deep surgical procedures, it is necessary to operate through a small opening into the body. These surgeries commonly employ specula (medical instruments for dilating a bodily passage or cavity) with built-in tubes to remove smoke from the surgical site during cautery procedures such as laser or electrosurgical excision or cauterization. Additionally, a separate suction tube and/or irrigation source may be introduced for the purpose of removing smoke and debris from, or irrigation of, the surgical site. Tubing used to remove smoke and debris or to provide irrigation can obstruct the surgical site and impede visualization. Therefore, it is preferable to avoid having these additional tubes at the surgical site.

Systems used in electrosurgical cautery procedures (referred to herein as cautery procedures) typically comprise a handpiece and interchangeable electrodes. Cautery electrodes consist of a tip that contacts tissue at the surgical site, a shaft of a given length, and a connector end that is inserted into the handpiece. The tips are made in many different shapes and sizes, including blade, ball tip, needle tip, and thin wire loops.

Prior art cautery systems that provide evacuation and/or irrigation have a variety of disadvantages. For example, cautery devices with incorporated suction were previously described in U.S. Pat. No. 2,888,928 to Seiger, U.S. Pat. No. 3,828,780 to Morrison, and U.S. Pat. No. 4,562,838 to Walker. These devices comprise a hollow metal conductive tube covered by insulation. The hollow inner metal tube carries the suction and ends in a blunt tip. This design is limited to a single tip that can perform coagulation but not cutting and requires a disposable handpiece with a smoke evacuation channel running through the handpiece.

U.S. Pat. No. 5,234,428 to Kaufman, U.S. Pat. No. 5,242,442 to Hirschfeld, and U.S. Pat. No. 8,057,470 to Lee et al. describe devices that include a smoke suction tube that surrounds or is applied next to a standard detachable electrode or blade. These devices also require a disposable handpiece with a smoke evacuation channel running through the handpiece.

Other patents for cautery systems with incorporated smoke evacuation include U.S. Pat. No. 5,836,944 to Cosmescu, U.S. Pat. No. 5,224,944 to Elliott, and U.S. Pat. No. 6,146,353 to Platt. These patents describe a moveable or detachable shroud or tube that covers or lies next to the cautery electrode and provides the smoke evacuation conduit. Exchanging of electrodes to provide different tips requires removal and/or adjustment and readjustment of the smoke evacuation conduit.

Therefore, it would be desirable to provide a cautery electrode and cautery system that overcome the aforementioned and other disadvantages.

SUMMARY OF THE INVENTION

One aspect of the present invention is a cautery electrode comprising an insulated shaft and a conductive element. The insulated shaft comprises first and second channels disposed within the shaft and extending the length of the shaft. The conductive element comprises a tip segment, a mid-segment, and an electrical contact segment. The conductive element is disposed within the first channel such that the tip segment extends from a distal end of the shaft, the mid-segment is within the shaft, and the electrical contact segment extends from a proximal end of the shaft.

Another aspect of the present invention is a cautery system comprising a cautery electrode and a connector having first, second, and third connection points. The cautery electrode comprises an insulated shaft and a conductive element. The insulated shaft comprises first and second channels disposed within the shaft and extending the length of the shaft. The conductive element comprises a tip segment, a mid-segment, and an electrical contact segment. The conductive element is disposed within the first channel such that the tip segment extends from a distal end of the shaft, the mid-segment is within the shaft, and the electrical contact segment extends from a proximal end of the shaft. A proximal portion of the cautery electrode is removably disposed within the connector at the first connection point such that the electrical contact segment of the cautery electrode is fully within the connector and a substantially air-tight connection is made between the insulated shaft and the connector.

Yet another aspect of the present invention is a method of performing a cautery procedure. In the method, a cautery electrode is attached to a connector; a cautery handpiece having an activator is attached to the connector; and a length of tubing is attached to the connector, the tubing in fluid communication with one or both of a vacuum source and an irrigation fluid source. The cautery handpiece is connected to an electrical source. The activator of the handpiece is operated, and a cautery procedure is performed.

The aforementioned and other features and advantages of the invention will become further apparent from the following detailed description of the presently preferred embodiments, read in conjunction with the accompanying drawings, which are not to scale. The detailed description and drawings are merely illustrative of the invention, rather than limiting, the scope of the invention being defined by the appended claims and equivalents thereof.

BRIEF DESCRIPTION OF THE DRAWINGS

FIG. 1A is a perspective view of a cautery system in accordance with the present invention;

FIG. 1B is an exploded view of the system of FIG. 1A;

FIG. 1C is an enlarged view of a portion of the cautery electrode illustrated in FIGS. 1A and 1B;

DETAILED DESCRIPTION OF THE PRESENTLY PREFERRED EMBODIMENTS

One aspect of the present invention is a cautery electrode. Cautery electrodes in accordance with the present invention are illustrated in FIGS. 1A and 1B as elements of a cautery system and in FIGS. 2A-2F independent of the system. Each cautery electrode comprises an insulated shaft 110 and a conductive element 120.

As illustrated in FIGS. 1A, 1B, and 2A-2F, shaft 110 is an elongated, substantially cylindrical member. The length of shaft 110 is variable depending on the intended use of the cautery electrode; the shaft must extend out from a connector 130 just far enough to allow space for flow of suction or irrigation when the cautery electrode is properly seated in connector 130 and a cautery handpiece 140, as described below. The shaft need not be cylindrical, with virtually any elongated shape being acceptable. Because the conductive element disposed within shaft 110 is electrically conductive, the shaft is made of an insulating (e.g., dielectric or nonconductive) material having sufficient rigidity to allow the tip segment of the cautery electrode to be applied to tissue appropriately during a surgical procedure. The insulating shaft shields from inadvertent lateral burning of tissue along the sides of the cautery electrode. This is especially important with elongated electrodes for deep procedures in body cavities. The insulating material is typically molded plastic or heat-shrink tubing. Suitable materials include elastomers and polymers such as polydimethylsiloxane (PDMS), polymethylmethacrylate (PMMA), polycarbonate, polytetrafluoroethylene (PTFE), polyvinylchloride (PVC), polysulfone, polystyrene, polymethylpentene, polypropylene, polyethylene, polyvinylidine fluoride, ABS (acrylonitrile-butadiene-styrene copolymer), cyclic-olefin polymer (COP), cyclic-olefin copolymer (COC), and other insulating materials that prevent or minimize conduction of both heat and electricity. The shaft may be, for example, an extruded or molded plastic tubing having multiple channels formed during the extrusion or molding process.

Figure 3A:
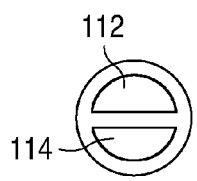
FIGS. 3A-3C provide cross-sectional views of a shaft of a cautery electrode in accordance with the present invention.
Figure 3B:
Figure 3C:

Shaft 110 includes at least a first channel 112 and a second channel 114. First channel 112 is substantially occupied by conductive element 120. Second channel 114 is open the entire length of the shaft and available for suction and/or irrigation supplied, for example, by a length of tubing 150 with which channel 114 is in fluid communication. Channels 112 and 114 are covered channels (i.e., lumens) that extend the entire length of shaft 110. FIGS. 3A-3C show various possible cross-sectional views of shaft 110, with channels 112 and 114 indicated in FIG. 3A. One skilled in the art will appreciate that FIGS. 3A-3C represent just a few of many possible cross-sectional configurations.

Conductive element 120 comprises a tip segment 122, a mid-segment 124, and an electrical contact segment 126, all of which can be seen in FIG. 1A. Tip segment 122 may assume a variety of different shapes such as, for example, a thin wire loop (FIGS. 1A and 1C at 122 and FIG. 2A at 122a) or blade tip (FIGS. 2D and 2F at 122d) for cutting, a ball tip (FIG. 2B at 122b) for coagulation after cutting, or a needle tip (FIGS. 2C and 2E at 122c) for transfer of concentrated energy into a limited area. Other shapes are, of course, possible. As is evident from FIGS. 2A-2F, each cautery electrode according to the current invention has a single tip shape. The entire cautery electrode can be exchanged for another cautery electrode during a surgical procedure if a different tip shape is desired. Mid-segment 124 and electrical contact segment 126 are typically a stainless steel rod or wire but may, alternatively, be constructed using any conductive material capable of heating the tip of the cautery electrode to an appropriate temperature for performing a cautery procedure (e.g., between approximately 350° C. and 1200° C.). Tip segment 122 may be constructed of the same material as the mid-segment and electrical contact segment; loop tips are also commonly fabricated from tungsten wire.

Figure 2A:
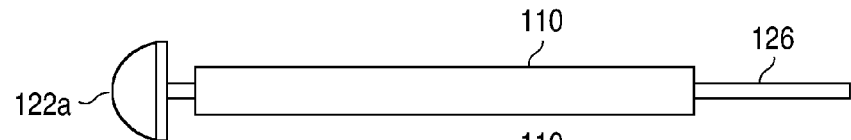
FIG. 2A is a perspective view of a cautery electrode in accordance with the present invention, the cautery electrode having a thin wire loop tip.
Figure 2B:
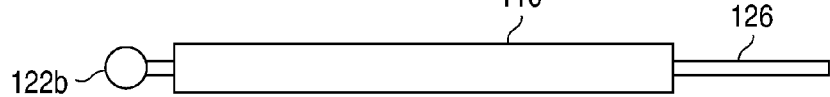
FIG. 2B is a perspective view of a cautery electrode in accordance with the present invention, the cautery electrode having a ball tip.
Figure 2C:
FIG. 2C is a perspective view of a cautery electrode in accordance with the present invention, the cautery electrode having a needle tip.
Figure 2D:
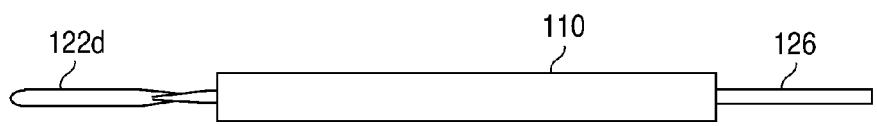
FIG. 2D is a perspective view of a cautery electrode in accordance with the present invention, the cautery electrode having a blade tip.
Figure 2E:
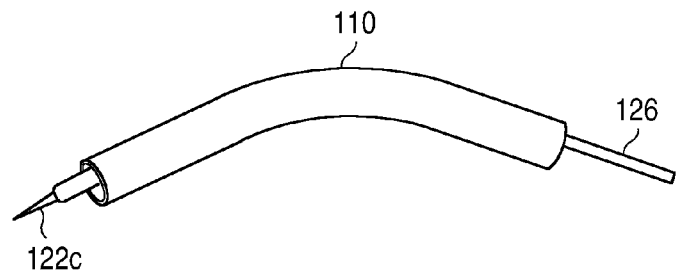
FIG. 2E is a perspective view of a cautery electrode in accordance with the present invention, the cautery electrode shown curved.
Figure 2F:
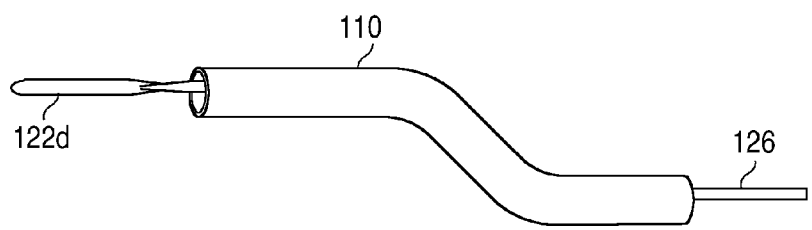
FIG. 2F is a perspective view of a cautery electrode in accordance with the present invention, the cautery electrode shown angled.

As seen in FIG. 1A, conductive element 120 is disposed in channel 112 such that tip segment 122 extends from a distal end of shaft 110, mid-segment 124 is within shaft 110, and electrical contact segment 126 extends from a proximal end of shaft 110. (The term "distal" is used herein to designate an end or portion nearest to the patient during use of the cautery electrode, and the term "proximal" is used herein to designate an end or portion nearest to the operator during use of the cautery electrode.) During fabrication of the cautery electrode, conductive element 120 may be positioned in shaft 110 by being inserted into a fully formed shaft. Alternatively, where shaft 110 is an extruded or molded plastic tubing having multiple channels formed during the extrusion or molding process, the tubing may be extruded or molded directly over conductive element 120. Extrusion or molding of the shaft over the conductive element is particularly convenient where the mid-segment of the cautery electrode is curved or angled as seen in FIGS. 2E and 2F, respectively.

Another aspect of the present invention is a cautery system that is formed when a connector 130 serves as a common hub to bring together a cautery electrode such as has been described above, a cautery handpiece 140, and a length of tubing 150. In the system, both the cautery electrode and handpiece 140 are removably attached to connector 130. The system may include multiple interchangeable cautery electrodes to offer a variety of different cautery tips such as can be seen in FIGS. 2A-2F. As illustrated in FIGS. 1A and 1B, connector 130 is a T-connector having first, second, and third connection points 132, 134, and 136, respectively. While connector 130 is shown to have three connection points, the connector may, alternatively, have more than three connection points and may assume shapes other than that of the T-connector shown in FIGS. 1A and 1B. For example, connector 130 could be a Y-connector. Connector 130 is preferably made of a soft rubber or plastic material but can be made of other materials that are conformable to one or both of the shaft 110 of the cautery electrode and the handpiece 140. Connector 130 is of sufficient size to adapt to different sizes and shapes of standard cautery handpieces.

As indicated in FIGS. 1A and 1B, a proximal portion of the cautery electrode is removably disposed within connector 130 at connection point 132 such that electrical contact segment 126 of the cautery electrode is fully within connector 130 and a substantially air-tight connection is made between shaft 110 and connector 130. Connection point 132 is illustrated in FIGS. 1A and 1B as a female connection point; however, it will be appreciated that shaft 110 could be constructed such that a portion of shaft 110 fits over a male connection point 132 rather than within a female connection point 132.

A distal portion of cautery handpiece 140 is removably disposed within connection point 134 such that a substantially air-tight connection is made between the cautery handpiece and the connector and such that electrical contact segment 126 of the cautery electrode is inserted into cautery handpiece 140, thereby providing an electrical connection between the cautery electrode and cautery handpiece 140. The cautery handpiece may be any commercially available handpiece and may be, for example, either hand activated or foot activated. Thus, it is preferable that connection point 134 be a female connection point that can be slipped over the distal end of the desired handpiece. As mentioned previously, connector 130 may be constructed of a soft rubber or plastic, making the connector readily adaptable to various shapes and sizes of handpieces.

One end of a length of tubing 150 is either removably or permanently attached to connector 130 at connection point 136, which may be either a male (as illustrated) or female connection point. The other end of tubing 150 is attached to, for example, a vacuum source or an irrigation fluid source. Connector 130, the cautery electrode, and/or tubing 150 may be adapted such that both a vacuum source and an irrigation fluid source may be simultaneously connected to the cautery electrode via connector 130. Thus, channel 114 of the cautery electrode may be in fluid communication with a vacuum and/or irrigation fluid source via tubing 150 and connector 130.

Yet another aspect of the present invention is a method of performing a cautery procedure. The method includes attaching to a connector, in any order, a first cautery electrode, a cautery handpiece having an activator, and a first length of tubing that is in fluid communication with one or both of a vacuum source and an irrigation fluid source. The cautery handpiece is connected to an electrical source either before or after the handpiece is attached to the connector. The resulting cautery system is then activated by operating the activator of the handpiece (for example, either a hand or foot activator), and the system is used to perform a cautery procedure. The method may further comprise removing the first cautery electrode from the connector and attaching a second cautery electrode to the connector. This step may be performed without removing the cautery handpiece from the connector and also without removing the attached tube(s) from the connector. The method may also further comprise attaching a second length of tubing to the connector if both vacuum and irrigation are desired, the second length of tubing in fluid communication with one or both of a vacuum source and an irrigation fluid source.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A cautery electrode, comprising:
   an insulated shaft comprising first and second channels disposed within the shaft and extending the length of the shaft; and
   a conductive element comprising a tip segment, a mid-segment, and an electrical contact segment;
   wherein the conductive element is configured to be permanently fixed within and connected to at least a portion of the first channel such that the tip segment extends from a distal end of the shaft, the mid-segment is within the shaft, and the electrical contact segment extends from a proximal end of the shaft.

2. The cautery electrode of claim 1 wherein the insulated shaft is an elongated, substantially cylindrical member.

3. The cautery electrode of claim 1 wherein the insulated shaft comprises a dielectric material.

4. The cautery electrode of claim 1 wherein the insulated shaft comprises a nonconductive material.

5. The cautery electrode of claim 1 wherein the insulated shaft comprises a material selected from the group consisting of polydimethylsiloxane (PDMS), polymethylmethacrylate (PMMA), polycarbonate, polytetrafluoroethylene (PTFE), polyvinylchloride (PVC), polysulfone, polystyrene, polymethylpentene, polypropylene, polyethylene, polyvinylidine fluoride, ABS (acrylonitrile-butadiene-styrene copolymer), cyclicolefin polymer (COP), cyclic-olefin copolymer (COC), and combinations thereof.

6. The cautery electrode of claim 1 wherein the insulated shaft consists of an extruded or molded plastic tubing.

7. The cautery electrode of claim 6 wherein the tubing is extruded or molded directly over the conductive element.

8. The cautery electrode of claim 1 wherein the insulated shaft further comprises a third channel disposed within the shaft and extending the length of the shaft.

9. The cautery electrode of claim 1 wherein the mid-segment and electrical contact segment comprise an electrically conductive material capable of heating the tip segment of the cautery electrode to between 350° C. and 1200° C.

10. The cautery electrode of claim 1 wherein the mid-segment is one or both of curved and angled.

11. The cautery electrode of claim 1 wherein the tip segment includes one of a wire loop tip, a blade tip, a ball tip, and a needle tip.

12. A cautery system, comprising:
    a first cautery electrode comprising an insulated shaft and a conductive element, the insulated shaft comprising first and second channels disposed within the shaft and extending the length of the shaft, the conductive element comprising a tip segment, a mid-segment, and an electrical contact segment, wherein the conductive element is configured to be permanently fixed within and connected to at least a portion of the first channel such that the tip segment extends from a distal end of the shaft, the mid-segment is within the shaft, and the electrical contact segment extends from a proximal end of the shaft; and
    a connector having first, second, and third connection points;
    wherein a proximal portion of the first cautery electrode is removably disposed within the connector at the first connection point such that the electrical contact segment of the cautery electrode is fully within the connector and a substantially air-tight connection is made between the insulated shaft and the connector.

13. The cautery system of claim 12 further comprising:
    a cautery handpiece, wherein a distal portion of the cautery handpiece is removably disposed within the connector at the second connection point such that a substantially air-tight connection is made between the cautery handpiece and the connector and such that the electrical contact segment of the cautery electrode is inserted into the cautery handpiece, thereby providing an electrical connection between the cautery electrode and the cautery handpiece.

14. The cautery system of claim 13 wherein the connector comprises a material conformable to one or both of the cautery electrode and the cautery handpiece.

15. The cautery system of claim 13 further comprising:
a length of tubing, wherein a first end of the length of tubing is attached to the connector at the third connection point.

16. The cautery system of claim 15 wherein a second end of the length of tubing is removably attached to one or both of a vacuum source and an irrigation fluid source.

17. The cautery system of claim 12 further comprising:
a second cautery electrode comprising an insulated shaft and a conductive element, the insulated shaft comprising first and second channels disposed within the shaft and extending the length of the shaft, the conductive element comprising a tip segment, a midsegment, and an electrical contact segment, wherein the conductive element is fixedly disposed within the first channel such that the tip segment extends from a distal end of the shaft, the mid-segment is within the shaft, and the electrical contact segment extends from a proximal end of the shaft; wherein the second cautery electrode is interchangeable with the first cautery electrode.

18. A method of performing a cautery procedure, the method comprising:
attaching a first cautery electrode to a connector, the first cautery electrode comprising an insulated shaft and a conductive element, the insulated shaft comprising first and second channels disposed within the shaft and extending the length of the shaft, the conductive element comprising a tip segment, a mid-segment, and an electrical contact segment, wherein the conductive element is configured to be permanently fixed within and connected to at least a portion of the first channel such that the tip segment extends from a distal end of the shaft, the mid-segment is within the shaft, and the electrical contact segment extends from a proximal end of the shaft;
attaching a cautery handpiece to the connector, the handpiece having an activator;
attaching a first length of tubing to the connector, the tubing in fluid communication with one or both of a vacuum source and an irrigation fluid source;
connecting the cautery handpiece to an electrical source;
operating the activator of the handpiece; and
performing a cautery procedure.

19. The method of claim 18, the method further comprising:
removing the first cautery electrode from the connector; and
attaching a second cautery electrode to the connector, the second cautery electrode comprising an insulated shaft and a conductive element, the insulated shaft comprising first and second channels disposed within the shaft and extending the length of the shaft, the conductive element comprising a tip segment, a mid-segment, and an electrical contact segment, wherein the conductive element is fixedly disposed within the first channel such that the tip segment extends from a distal end of the shaft, the mid-segment is within the shaft, and the electrical contact segment extends from a proximal end of the shaft.

20. The method of claim 18, the method further comprising:
attaching a second length of tubing to the connector, the second length of tubing in fluid communication with one or both of a vacuum source and an irrigation fluid source.

* * * * *

(12) EX PARTE REEXAMINATION CERTIFICATE (176th)
Ex Parte Reexamination Ordered under 35 U.S.C. 257

United States Patent
Zinnanti

(10) Number: US 9,101,363 C1
(45) Certificate Issued: Aug. 11, 2020

(54) CAUTERY ELECTRODE WITH MULTI-CHANNEL INSULATED SHAFT

(71) Applicant: William J. Zinnanti, Santa Cruz, CA (US)

(72) Inventor: William J. Zinnanti, Santa Cruz, CA (US)

Supplemental Examination Request:
No. 96/000,288, Apr. 12, 2019

Reexamination Certificate for:
Patent No.: 9,101,363
Issued: Aug. 11, 2015
Appl. No.: 13/706,242
Filed: Dec. 5, 2012

Related U.S. Application Data

(60) Provisional application No. 61/681,626, filed on Aug. 10, 2012.

(51) Int. Cl.
*A61B 18/14* (2006.01)

(52) U.S. Cl.
CPC .......... *A61B 18/14* (2013.01); *A61B 18/1482* (2013.01); *A61B 18/1402* (2013.01); *A61B 2018/144* (2013.01); *A61B 2018/1407* (2013.01); *A61B 2018/1417* (2013.01); *A61B 2218/002* (2013.01); *A61B 2218/007* (2013.01)

(58) Field of Classification Search
None
See application file for complete search history.

(56) References Cited

To view the complete listing of prior art documents cited during the supplemental examination proceeding and the resulting reexamination proceeding for Control Number 96/000,288, please refer to the USPTO's public Patent Application Information Retrieval (PAIR) system under the Display References tab.

*Primary Examiner* — Catherine S Williams

(57) ABSTRACT

The invention provides a cautery electrode comprising an insulated shaft and a conductive element. The insulated shaft includes first and second channels disposed within the shaft and extending the length of the shaft. The conductive element comprises a tip segment, a mid-segment, and an electrical contact segment. The conductive element is disposed within the first channel such that the tip segment extends from a distal end of the shaft, the mid-segment is within the shaft, and the electrical contact segment extends from a proximal end of the shaft. A cautery system includes the cautery electrode, a cautery handpiece, a length of tubing, and a connector having first, second, and third connection points. The cautery electrode and the cautery handpiece are removably attached to the connector at the first and second connection points, and the length of tubing is attached to the connector at the third connection point.

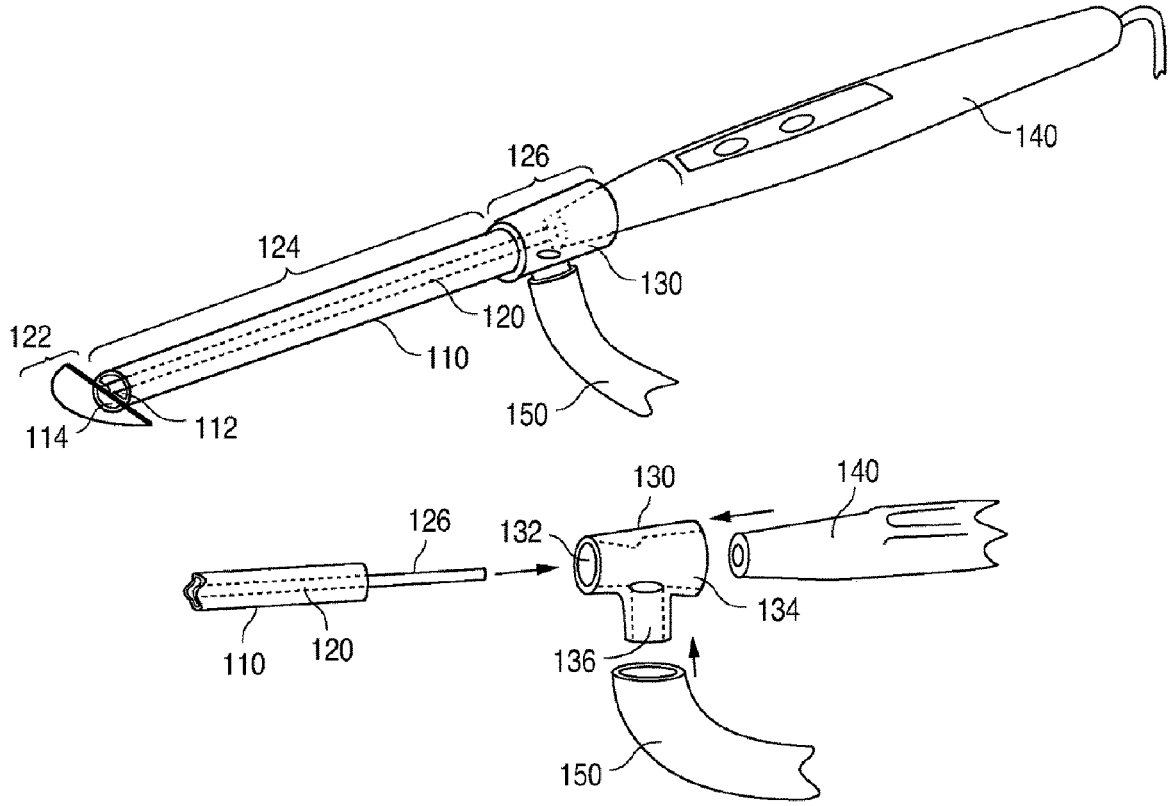

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-11 are cancelled.

Claims 12-13 and 18 are determined to be patentable as amended.

Claims 14-17 and 19-20, dependent on an amended claim, are determined to be patentable.

New claim 21 is added and determined to be patentable.

12. A cautery system, comprising:
a first cautery electrode comprising an insulated shaft and a conductive element, the insulated shaft comprising first and second channels disposed within the shaft and extending the length of the shaft, the conductive element comprising a tip segment, a mid-segment, and an electrical contact segment, wherein the conductive element is configured to be permanently fixed within and connected to at least a portion of the first channel such that the tip segment extends from a distal end of the shaft, the mid-segment is within the shaft, and the electrical contact segment extends from a proximal end of the shaft; [and]
a connector having first, second, and third connection points;
wherein a proximal portion of the first cautery electrode is removably disposed within the connector at the first connection point such that the electrical contact segment of the cautery electrode is fully within the connector and a substantially air-tight connection is made between the insulated shaft and the connector; *and*
*a cautery handpiece,*
*the electrode and the cautery handpiece each being removably, replaceably, and interchangeably coupled to the connector.*

13. The cautery system of claim 12 [further comprising: a cautery handpiece], wherein a distal portion of the cautery handpiece is removably disposed within the connector at the second connection point such that a substantially air-tight connection is made between the cautery handpiece and the connector and such that the electrical contact segment of the cautery electrode is inserted into the cautery handpiece, thereby providing an electrical connection between the cautery electrode and the cautery handpiece.

18. A method of performing a cautery procedure, the method comprising: *removably, replaceably, and interchangeably*
attaching a first cautery electrode to a connector, the first cautery electrode comprising an insulated shaft and a conductive element, the insulated shaft comprising first and second channels disposed within the shaft and extending the length of the shaft, the conductive element comprising a tip segment, a mid-segment, and an electrical contact segment, wherein the conductive element is configured to be permanently fixed within and connected to at least a portion of the first channel such that the tip segment extends from a distal end of the shaft, the mid-segment is within the shaft, and the electrical contact segment extends from a proximal end of the shaft; *removably, replaceably, and interchangeably* attaching a cautery handpiece to the connector, the handpiece having an activator; attaching a first length of tubing to the connector, the tubing in fluid communication with one or both of a vacuum source and an irrigation fluid source; connecting the cautery handpiece to an electrical source; operating the activator of the handpiece; and performing a cautery procedure.

*21. A cautery system, comprising:*
*a first cautery electrode, comprising: an insulated shaft comprising an outer tube and interior structure defining at least first and second channels disposed within the shaft and extending the length of the shaft, the shaft having a proximal end and a distal end and the at least first and second channels each having a proximal end and a distal end; and a conductive element comprising a tip segment, a mid-segment, and an electrical contact segment; wherein the conductive element is configured to be permanently fixed within and connected to at least a portion of the first channel such that the tip segment extends from the distal end of the shaft, the mid-segment is within the shaft, and the electrical contact segment extends from a proximal end of the shaft, wherein the at least first and second channels terminate in openings at the proximal end, and wherein the proximal ends of the outer tube and the at least first and second channels are substantially coterminous, to facilitate coupling of the electrode to at least one of a connector and to a handpiece;*
*a connector having at least first and second connection points;*
*wherein a proximal portion of the first cautery electrode is disposed within the connector at the first connection point such that the electrical contact segment of the cautery electrode is fully within the connector and a substantially air-tight connection is made between the insulated shaft and the connector; and*
*a cautery handpiece, at least one of the electrode and the connector each being removably, replaceably, and interchangeably coupled to the cautery handpiece.*

* * * * *